United States Patent [19]

Kagawa

[11] Patent Number: 5,222,937
[45] Date of Patent: Jun. 29, 1993

[54] ULTRASONIC TREATMENT APPARATUS

[75] Inventor: Hiroaki Kagawa, Tokyo, Japan

[73] Assignee: Olympus Optical Co., Ltd., Tokyo, Japan

[21] Appl. No.: 775,785

[22] Filed: Oct. 11, 1991

[30] Foreign Application Priority Data

Jan. 11, 1991 [JP] Japan .................................. 3-1993

[51] Int. Cl.⁵ .............................................. A61B 17/20
[52] U.S. Cl. .................................. 604/22; 128/24 AA; 606/169
[58] Field of Search ....................... 128/24 AA; 604/22; 606/169, 171

[56] References Cited

U.S. PATENT DOCUMENTS

| | | | |
|---|---|---|---|
| 3,990,452 | 11/1976 | Murry et al. | 128/24 AA |
| 4,169,984 | 10/1979 | Parisi | 128/24 AA |
| 4,330,278 | 5/1982 | Martin | 128/24 AA |
| 4,535,759 | 8/1985 | Polk et al. | |
| 4,561,438 | 12/1985 | Bonnet et al. | 128/24 AA |
| 4,634,419 | 1/1987 | Kreizman et al. | 604/22 |
| 4,646,725 | 3/1987 | Moasser | |
| 4,816,018 | 3/1989 | Parisi | 128/24 AA |
| 4,974,581 | 12/1990 | Wiksell | 604/22 |
| 4,989,588 | 2/1991 | Kubota et al. | 604/22 |
| 5,038,756 | 8/1991 | Kepley | 128/24 AA |
| 5,163,433 | 11/1992 | Kagawa et al. | 604/22 |

FOREIGN PATENT DOCUMENTS

| | | |
|---|---|---|
| 3520133 | 12/1986 | Fed. Rep. of Germany . |
| 61-159953 | 7/1986 | Japan . |
| 62-207450 | 9/1987 | Japan . |
| 64-9015 | 2/1989 | Japan . |
| 1391631 | 4/1988 | U.S.S.R. . |
| 1438745 | 11/1988 | U.S.S.R. . |

Primary Examiner—Stephen C. Pellegrino
Assistant Examiner—Michael Rafa
Attorney, Agent, or Firm—Frishauf, Holtz, Goodman & Woodward

[57] ABSTRACT

An ultrasonic treatment apparatus includes an ultrasonic vibration generating portion for generating ultrasonic vibrations, an amplifying portion for amplifying the ultrasonic vibrations generated by the ultrasonic vibration generating portion, a vibration transmitting member for transmitting the ultrasonic vibrations amplified by the amplifying portion, and a connecting member for connecting the vibration transmitting member to the amplifying portion such that the central axes of the vibration transmitting member and of the amplifying portion intersect at a predetermined angle. The generated ultrasonic vibration includes nodes and loop portions between adjacent nodes, and both a connecting portion between the connecting member and the amplifying portion and a connection portion between the connecting member and the vibration transmitting member are formed in the vicinity of a position at which a loop portion of the ultrasonic vibration lies.

23 Claims, 7 Drawing Sheets

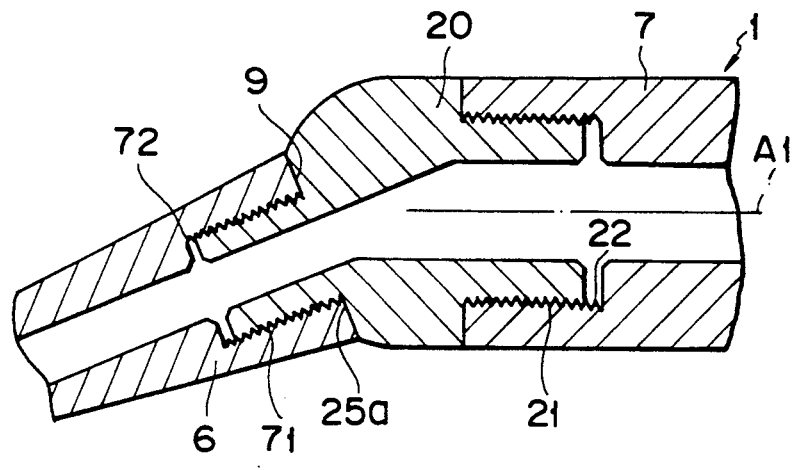
F I G. 10
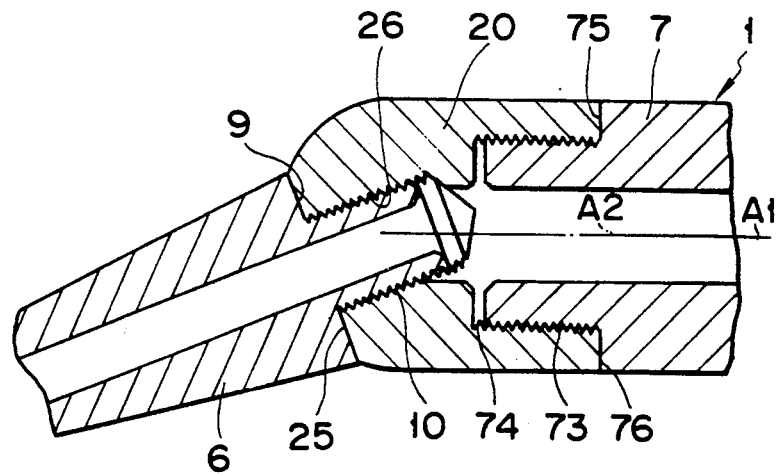
F I G. 11

ULTRASONIC TREATMENT APPARATUS

BACKGROUND OF THE INVENTION

Field of the Invention

This invention relates to an ultrasonic treatment apparatus which is used for curing affected parts of living bodies by means of ultrasonic vibrations.

Description of the Related Art

A typical ultrasonic treatment apparatus which is used for curing affected parts of living bodies is disclosed in Japanese Laid-open Patent Application Publication 61-159953. In the ultrasonic treatment apparatus of this type, a treatment probe which transmits ultrasonic vibrations is made from a metallic pipe and has a proximal end connected to an ultrasonic vibrator and a distal end used as a working end.

In the medical treatment, the affected part of a living body is pushed by the distal end of the probe and the vibrator is operated at a driving frequency with a loop of the ultrasonic vibrations located at the distal end, whereby living tissues of the affected part are emulsified or cut off by the oscillated distal end of the probe.

Improved ultrasonic treatment apparatuses which each have a high operativeness in a body cavity are disclosed in Japanese Laid-open Patent Application Publication 62-207450 and U.S. Pat. No. 4,634,419, for example. Each of these apparatuses has a probe with a bent distal end portion. The probe is formed by bending a straight pipe element at a required angle, by cutting the abutted end faces of two straight pipes slantwise with respect to the axis of them, or by fixing together two straight pipes at their ends by a screw, by welding or by means of other connecting means.

However, this bent probe faces the following problems. When a straight pipe is physically bent at a required angle, cracks and/or distortion is produced at the bent portion and thus the fatigue strength of the probe is lowered remarkably whereby the probe is likely to be easily broken. In order to avoid this problem, the amplitude of the vibration at which the bent probe is used must be limited to a small value, requiring a long operation time. Otherwise, the probe is apt to be broken during the operation. When the bent probe is formed by welding two abutted pipes and by cutting them slantwise, this problem is solved. However, this type of bent probe causes another problem in that it is not easy to remove the probe from the ultrasonic vibrator and replace it with a new one.

SUMMARY OF THE INVENTION

The object of this invention is to provide an ultrasonic treatment apparatus which is provided with freely replaceable probes having different bent angles, which has a high fatigue strength against ultrasonic vibration and which also has a long life.

The object is attained by providing an ultrasonic treatment apparatus which comprises ultrasonic vibration generating means for generating an ultrasonic vibration, amplifying means having a central axis for amplifying the ultrasonic vibration generated by the ultrasonic vibration generating means, vibration transmitting means having a central axis for transmitting the ultrasonic vibration amplified by the amplifying means to objective parts of living bodies, and connecting means for connecting the vibration transmitting means to the amplifying means such that the axes of the vibration transmitting means and the amplifying means make a predetermined angle and a loop of the ultrasonic vibration lie in the vicinity of the connecting portions between the connecting means and the amplifying means and between the connecting means and the vibration transmitting means.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 10 and 11 are longitudinal cross-sectional views of the main parts of modifications of the second embodiment;

DETAILED DESCRIPTION OF THE PREFERRED EMBODIMENTS

This invention will now be described by way of embodiments and modifications thereof with reference to the accompanying drawings.

Figure 1:
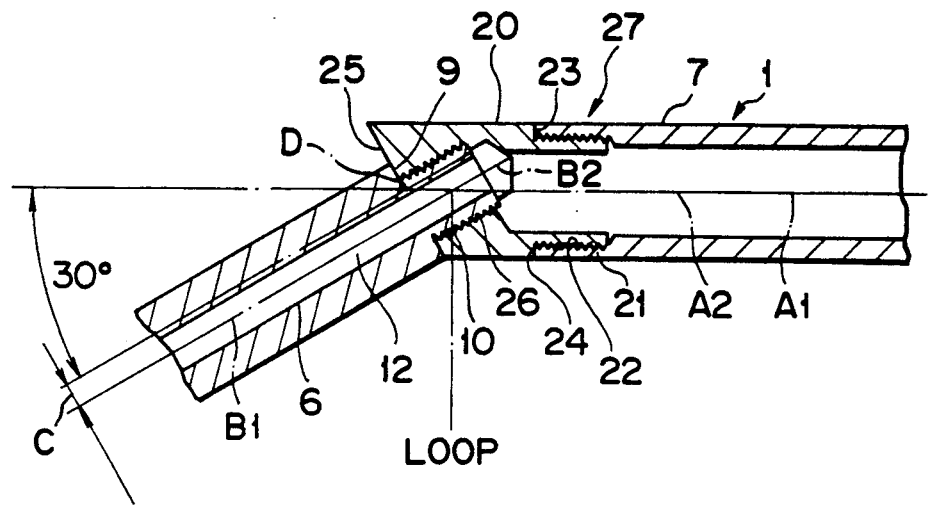
FIGS. 1 and 2 are a longitudinal cross-sectional view and a side view of the main part of the first embodiment of an ultrasonic treatment apparatus according to this invention, respectively.
Figure 2:
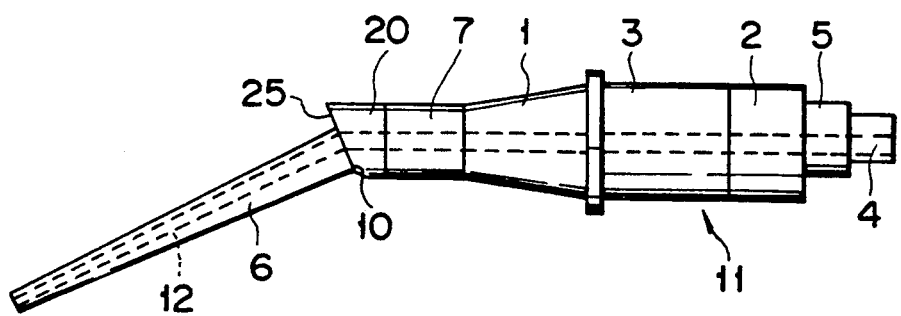

FIGS. 1 and 2 show an ultrasonic treatment apparatus according to the first embodiment of this invention.

As shown in FIG. 2, the ultrasonic treatment apparatus has an ultrasonic vibration generating portion 11 which comprises a horn 1 used as a front plate, a back plate 2 and a piezoelectric element 3 sandwiched between them. The piezoelectric element 3 is tightened by means of a bolt 4 and a nut 5 at such a torque that the element 3 is operated at a constant vibration characteristic.

On the distal end of the horn 1 is formed a cylindrical portion 7 which has a distal end connected to a probe 6 by means of a removable connecting member 20. In other words, as shown in FIG. 1, the connecting member 20 is cylindrical and is formed on its proximal end with a male screw 21 so as to be concentrically with the central axis A2 of the member 20. A female screw 22 is formed concentrical with the central axis A1 of the horn 1 in the distal end portion of the cylindrical portion 7 and is screwed into the male screw 21.

The proximal end of the male screw 21 formed on the connecting member 20 defines an aligning face 23 perpendicular to the central axis A2 of the connecting member 20. The distal end face 24 of the cylindrical portion 7 is perpendicular to the central axis A1 of the horn 1. In this connection, when the male screw 21 is screwed into the female screw 22, the aligning face 23 of the connecting member 20 abuts against the distal face 24 of the horn 1 and is fixed thereto so that the central axis A2 of the connecting member 20 is aligned with the central axis A1 of the horn 1.

The connecting member 20 has a distal face 25 which is inclined at an angle of 60 degrees, for example, with respect to the central axis A2 of the connecting member 20. In the distal end portion of the connecting member 20 is formed a female screw 26 perpendicular to the distal end 25. The central axis B1 of the female screw 26 is offset downward by a distance C from the coinciding point D of the central axis A2 of the connecting member 20 with the distal face 25, and the central axis A2 of the connecting member 20 and the central axis B2 of the female screw 26 coincide with each other in the connecting member 20.

A male screw 10 formed on the probe 6 is screwed into a female 26 of the connecting member 20, and an aligning face 9 formed on the proximal end of the male screw 10 of the probe 6 abuts against the distal face 25 of the connecting member 20 and is fixed thereto. Since the male screw 10 is concentric with the central axis B1 of the probe 6 at its proximal end portion, the central axis B1 of the probe 6 is aligned with the central axis B2 of the female screw 26, and the central axes A2 and B1 intersect in the connecting member 20. A loop of ultrasonic vibrations is made to lie on the coinciding point. In other words, the loop of the vibrations transmitted from the vibration generating portion 11 is produced at a portion which is displaced from the distal face 25 of the connecting member 20 toward its proximal end. The connecting portion 27 between the horn 1 and the connecting member 20 can be provided at a portion which is separated from the loop lying portion by the distance of or less than $\lambda/4$ ($\lambda$ being a wavelength). In this case, however, the screw-connected portion is likely to be broken by stresses produced by the ultrasonic vibrations. Therefore, when the vibrations have such a large amplitude as 100 to 300 $\mu$m, it is preferred that the connecting portion 27 is formed in the vicinity of the loop-lying portion at which the generated stresses are relatively small.

In this ultrasonic treatment apparatus, the connecting member 20 is readily removed from the horn 1, and thus a not-bent probe 6 is attached to the horn 1 by removing the connecting member 20.

Alternatively, connecting members 20 bent at different angles are prepared and the one which has the suitable angle can be attached to the probe 6. The total length is the same as the length when the probe is directly connected to the horn without using the connecting member 20, avoiding the lowering of the operativeness due to an undue total length of the apparatus.

A suck-in hole 12 communicating with an absorbing device (not shown) extends through the probe 6, the horn 1, the piezoelectric element 3 and the bolt 4.

Figure 3:
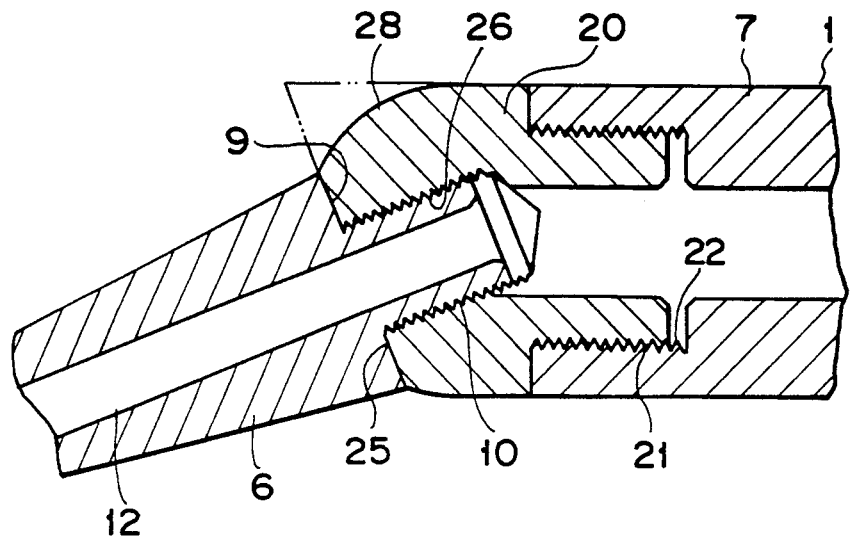
FIG. 3 is a longitudinal cross-sectional view of the second embodiment of an ultrasonic treatment apparatus according to this invention.

FIG. 3 shows the second embodiment of this invention, in which the projection (shown by two-dot chain lines in FIG. 3) is cut off from the distal face 25 of the connecting member 20 so that a partially spherical portion 28 is formed there. Further, the facing ends of the connecting member 20 and the probe 6 have the same outer configuration so that the whole areas of the distal face 25 of the connecting member 20 and the aligning face 9 of the probe 6 contact with each other. The other structure is the same as that of the first embodiment.

This structure does not obstruct the view of field of an operator and allows for safe operation. Further, since the whole areas of the distal face 25 of the connecting member 20 and the aligning face 9 of the probe 6 contact with each other, the transmission efficiency of ultrasonic vibrations is improved.

Figure 4:
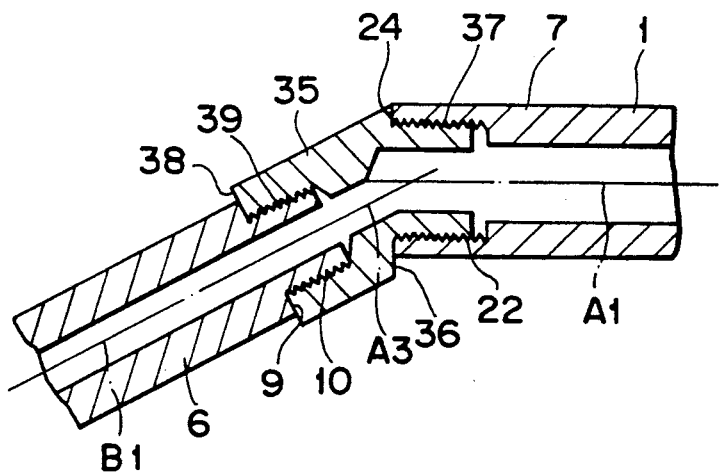
FIG. 4 is a longitudinal cross-sectional view of the third embodiment of an ultrasonic apparatus according to this invention.

FIG. 4 shows the third embodiment of this invention, in which the aligning face 36 of a connecting member 35 is inclined at 60 degrees, for example, with respect to the central axis B2 of the connecting member 35. On the connecting member 35 is formed a male screw 37 which is perpendicular to the aligning face 36 and is detachably screwed into a female screw 22 of the cylindrical portion 7 of the horn 1 so as to cause the aligning face 36 to abut against the distal face 24 of the horn 1.

The distal face 38 of the connecting member 35 so as to be perpendicular to the distal face 38 is made perpendicular to the central axis A3 of the connecting member 35. A female screw 39 is formed in the connecting member 35 and is connected by the male screw 10 of the probe 6 so that the central axis A3 of the connecting member 35 is aligned with the central axis B1 of the probe 6.

Figure 5:
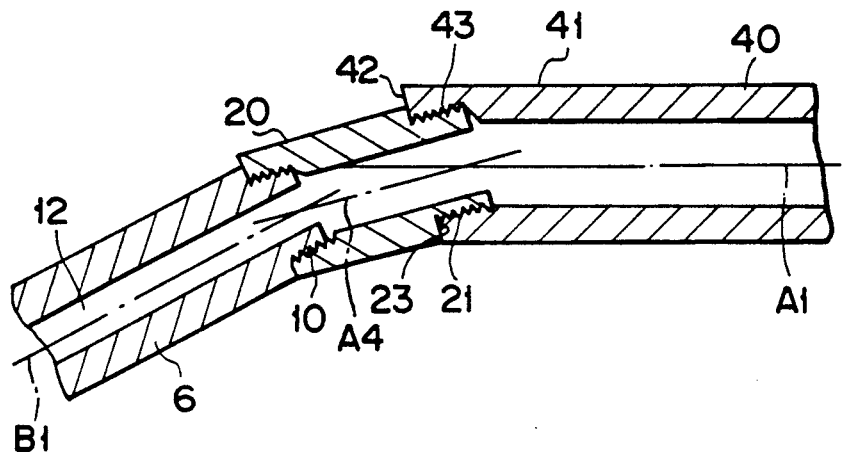
FIG. 5 is a longitudinal cross-sectional view of the fourth embodiment of an ultrasonic treatment apparatus according to this invention.

FIG. 5 shows the fourth embodiment.

In this embodiment, the distal face 42 of the cylindrical portion 41 of the horn 40 is inclined at 75 degrees, for example, with respect to the central axis A1 of the horn 40. Perpendicularly to the distal face 42 of the cylindrical portion 41 is formed a female screw 43 in which the male screw 21 of the connecting member 20 is threadably inserted. When the connecting member 20 is attached, the aligning face 23 of the connecting member 20 abuts against the distal face 42 of the horn 40. A probe 6 is connected to the distal end of the connecting member 20 at a predetermined angle similarly to the case of the first embodiment.

In this arrangement, the probe 6 is connected to the horn 40 in such a manner that the probe 6 is bent twice. Thus, the probe 6 of the fourth embodiment is bent more than the probe 6 of the first embodiment.

Figure 6:
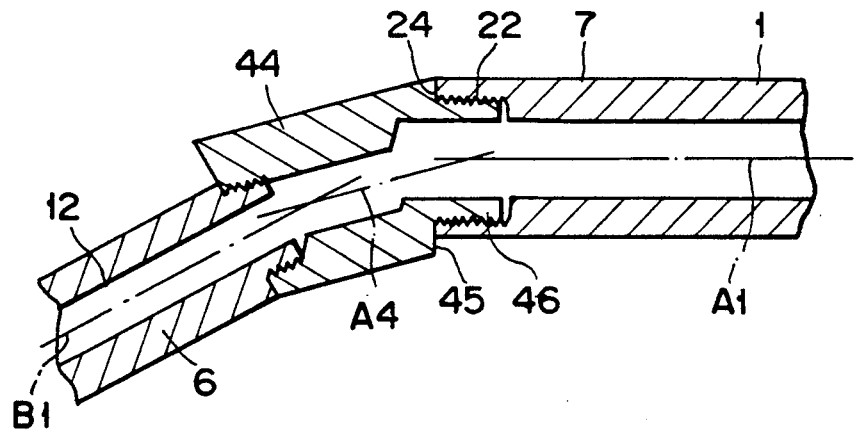
FIG. 6 is a longitudinal cross-sectional view of the fifth embodiment of an ultrasonic apparatus according to this invention.

FIG. 6 shows the fifth embodiment, in which the aligning face 45 of a connecting member 44 is inclined at 75 degrees, for example, with respect to the central axis A4 of the connecting member 44. The male screw 46 is formed perpendicular to the aligning face 45 and is screwed into the female screw 22 formed in the cylindrical portion 7 of the horn 1 so as to be concentric with the central axis A1 of the cylindrical portion 7, whereby the aligning face 45 of the connecting member 44 abuts against the distal face 24 perpendicular to the central axis A1 of the horn 1. A probe 6 is connected to the distal end of the connecting member 44 at a predetermined angle similarly to the case of the first embodiment.

Also in this arrangement, the probe 6 can be bent at a greater angle from the horn 1 than the probe 6 of the first embodiment. Further, since the distal face 24 of the cylindrical portion 7 of the horn 1 is perpendicular to the central axis A1 of the horn 1 and the female screw 22 is also perpendicular to the distal face 24, a not-bent probe 6 can be connected to the horn 1.

Figure 7:
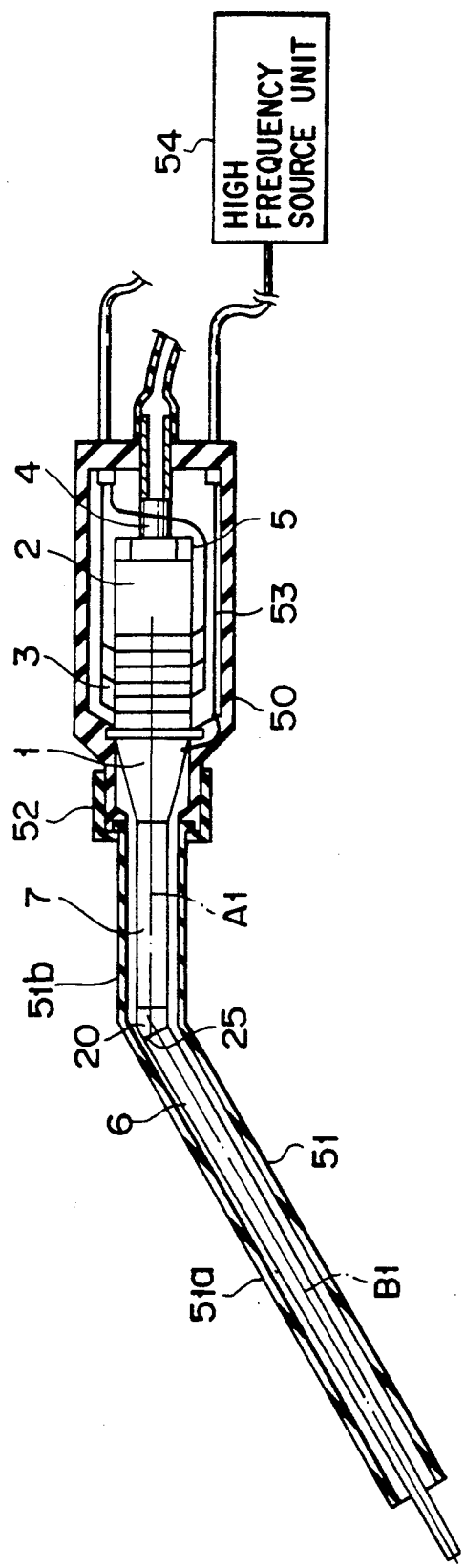
FIG. 7 is a longitudinal cross-sectional view of the sixth embodiment of an ultrasonic apparatus according to this invention.

FIG. 7 shows the six embodiment of this invention which comprises a vibrator cover 50 for covering the vicinity of the piezoelectric element 3 and the portion of the horn 1 except for its distal end portion, and a sheath 51 for covering the distal end portion of the horn 1 and the portion of the probe 6 except for its distal end portion. The vibrator cover 50 and the sheath 51 are made of electrically insulating material. The sheath 51 is formed by connecting pipes 51a and 51b in a bent manner. The vibrator cover 50 is detachably connected to the sheath 51 by means of a connecting ring 52.

To the horn 1 is connected cords 53 of a high frequency electrical source whose leading ends are connected to a high frequency source unit 54 by means of a connector (not shown. The structure of the sixth embodiment is otherwise similar to that of the first embodiment.

In the sixth embodiment, high frequency current produced from the high frequency source unit 54 can be transmitted to the horn 1 through the cords 53 of the high frequency electrical source and then to the connecting member 20 connected by the cords 53 and further to the probe 6 so that the distal end of the probe 6 is used as a high frequency treating electrode. To the high frequency electrical source unit 54 is connected an electrode (not shown) which is provided outside of a body cavity and which is coupled with the high frequency treating electrode.

In a case where blood is bleeding from living tissues during an operation, the bleeding tissues are coagulated to stop bleeding by causing high frequency current to flow from the probe 6.

Since the vibrator cover 50 and the sheath 51 covering the ultrasonic vibrator 3, the horn 1 and the probe 6 are made of electrically insulating material, high frequency current does not leak to the outer surface of the ultrasonic treatment apparatus, when the high frequency current is caused to flow from the high frequency source unit 54 through the horn 1, the connecting member 20 and the probe 6. In this respect, neither a patient nor an operator is shocked by electricity so that operation can be performed safely.

In the first to sixth embodiments, the connection between the connecting member and the probe may be made by welding, brazing or the like so that they form a body.

Figure 8:
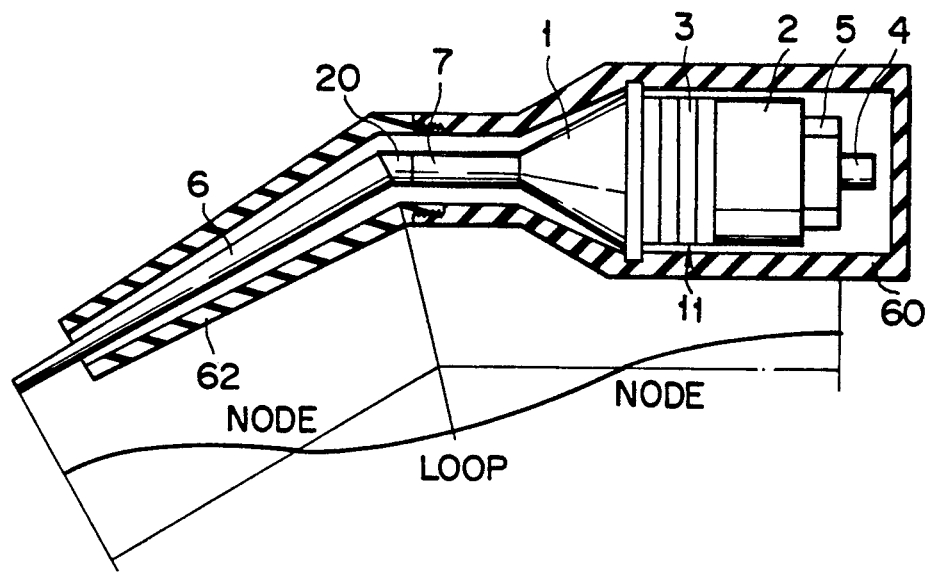
FIGS. 8 and 9 are a partially sectioned view and an exploded view of one modification of the first embodiment.

FIG. 8 shows a modification of the first embodiment of this invention in which the horn 1 and the probe 6 are connected by means of a short connecting member 20, the ultrasonic vibration generating portion 11 is covered with a main body cover 60 made of electrically insulating material, and the probe 6 except for its distal end portion is covered with a sheath 62 also made of electrically insulating material.

Figure 9:
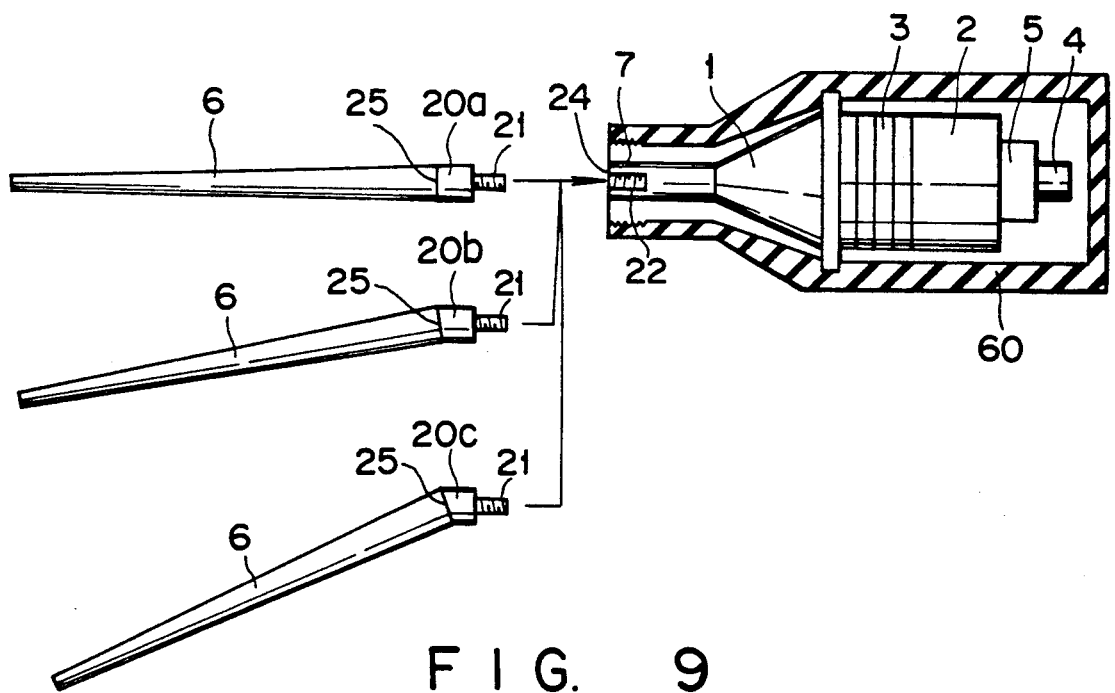

As shown in FIG. 9, the distal face 24 of the cylindrical portion 7 of the horn 1 is perpendicular to the central axis of the cylindrical portion 7 itself, and thus the probe 6 is connected to the horn 1 in an aligned manner. First, the sheath 62 is removed from the main body cover 60 and then the probe 6 is disconnected from the connecting member 20. Finally, the connecting member 20 is detached from the cylindrical portion 7 of the horn 1. In the reverse steps, the connecting member 20a and the probe 6 connected in an aligned manner may be joined to the cylindrical portion 7.

As shown in FIG. 9 again, the probe 6 may be mounted on the horn 1 at different angles with respect to the horn 1 by preparing connecting members 20b and 20c having distal faces inclined at different angles.

FIGS. 10, 11, 13 and 15 show modifications of the second embodiments of this invention.

In each of above embodiments and the modification thereof a female screw is formed in the distal end portion of the connecting member and a male screw is formed on the proximal end of the probe, with the latter screw being screwed into the former screw. However, the following arrangement is also possible.

In the first modification shown in FIG. 10, a male screw 71 is formed on the distal end portion of the connecting member 20 of the second embodiment so as to be perpendicular to the distal face 25. On the male screw 71 is threadably mounted a female screw 72 formed perpendicularly to the proximal face 9 in the proximal end portion of the probe 6 so that the proximal face 9 of the probe abuts against the distal face 25 of the connecting face 25. The structure is otherwise similar to that of the second embodiment.

In the second modification shown in FIG. 11, a female screw 74 is formed perpendicularly to a proximal face 76 in the proximal end portion of the connecting member 20 of the second embodiment. In the female screw 74 is threadably inserted a male screw 73 formed coaxial with the central axis A1 of the horn 1 in the cylindrical portion 7 of the horn 1 in such a manner that the distal face 76 of the connecting member 20 abuts against the aligning face 75 of the horn 1 and is fixed thereto. The structure is otherwise similar to that of the second embodiment.

Since, as shown in FIG. 11, the proximal face 76 of the connecting member 20 is perpendicular to the central axis A2 of the connecting member 20 and the female screw 74 in the proximal end portion of the connecting member 2 is concentrical with the central axis A2 of the connecting member 20, the central axis A2 of the connecting member 20 coincides with the central axis A1 of the horn 1. However, the proximal face 76 of the connecting member 20 may be inclined at 75 degrees, for example, with respect to the central axis A2 of the connecting member 20. In this case, the central axis A2 of the connecting member 20 makes an angle of 15 degrees with the central axis A1 of the horn 1, whereby the angle of bending between the probe 6 and the horn 1 becomes larger.

Figure 12:
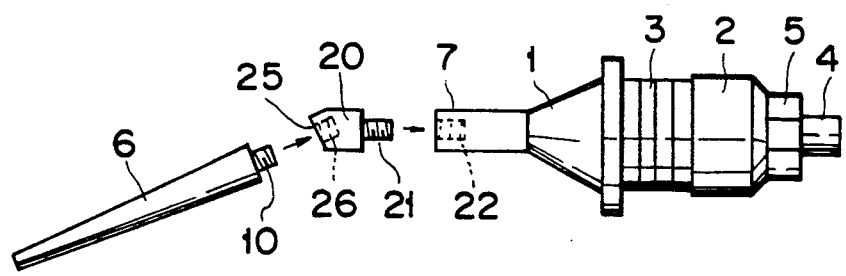
FIG. 12 is an exploded view of the second embodiment of the ultrasonic treatment apparatus.

FIG. 12 further shows the second embodiment in which the horn 1, the connecting member 20 and the probe 6 are detachably connected together in turn by means of screws. The bending angle of the probe 6 is readily changed by preparing only connecting members 20 having distal faces 25 inclined at different angles.

Figure 13:
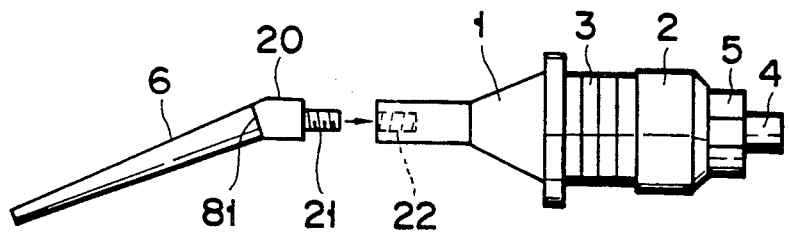
FIGS. 13 and 14 are exploded views of further modifications of the second embodiment.

FIG. 13 shows the third modification of the second embodiment. The connecting member 20 is fixed to the probe 20 at a connecting portion 81 by means of brazing, adhering, welding or the like, and the horn 1 is detachably connected to them by means of screws. Accordingly, the bending angle of the probe 6 can be easily changed by using probes 6 provided with connecting members 20 having distal faces inclined at different angles. Further, since the connecting member 20 is connected to the horn 1 at a single connecting portion, the apparatus is easily handled.

Figure 14:
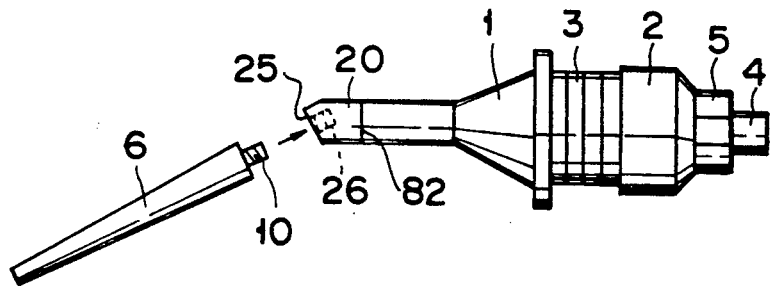

FIG. 14 shows the fourth modification of the second embodiment. The connecting member 20 is fixed to the horn 1 by means of brazing, adhering, welding or the like, and the probe 6 is detachably connected to them by means of screws. Although the bending angle of the hand piece is determined by the angle of the distal face 25 of the connecting member 20 to a fixed value, the ultrasonic vibrators each comprising the elements other than the bent connecting member 20, that is, the horn 1, the piezoelectric element 3, the back plate 2, the bolt 4 and the nut 5 can be mass-produced irrespective of the kinds of probes at a lower cost than the conventional ones.

The bending angle between the probe 6 and the horn 1 is selected to be 5 degrees to 60 degrees, preferably, 10 degrees to 45 degrees due the operativeness of the apparatus and the ultrasonic vibrators.

For abdominal operations in the field of digestive system surgery, the bending angle of 5 degrees to 30 degrees is suitable because the operating regions are not so limited. In the field of micro-surgery such as the neurosurgery, suitable angles are selected from the range of 15 degrees to 60 degrees depending upon the depths of the affected portions because the operating regions are much more limited.

The larger the bending angle, the larger the attenuation of ultrasonic vibrations transmitted to the distal end of the probe and the smaller the amplitude of the oscillation of the probe, lowering the cutting-off ability of tissues. The most part of the energy of the attenuated ultrasonic vibrations is changed into heat to raise the temperature of the ultrasonic vibrator, the probe and others. A large amount of cooling water must be caused to flow in order to cool them. For this reason a bending angle up to 60 degrees is suitable.

The invention is not limited to the above-described embodiments and modifications, but is applicable to further various modifications thereof which are within the spirit and scope of the invention as defined in the appended claims.

What is claimed is:

1. An ultrasonic treatment apparatus comprising:
    ultrasonic vibration generating means for generating an ultrasonic vibration having nodes and loop portions between adjacent nodes;
    amplifying means having a central axis for amplifying said ultrasonic vibration generated by said ultrasonic vibration generating means;
    vibration transmitting means having a central axis, for transmitting said ultrasonic vibration amplified by said amplifying means to objective parts of living bodies; and
    connecting means for connecting said vibration transmitting means to said amplifying means such that said central axes of said vibration transmitting means and of said amplifying means intersect with each other at a predetermined angle at an intersection point, wherein a loop portion of said ultrasonic vibration lies in a region including said intersection point, a connecting portion between said connecting means and said amplifying means, and a connecting portion between said connecting means and said vibration transmitting means.

2. The apparatus according to claim 1, wherein said connecting means includes means for detachably connecting said connecting means to said amplifying means.

3. The apparatus according to claim 2, wherein said connecting means includes one of a male screw and a female screw, and said amplifying means includes the other one of said male screw and said female screw, said male screw and said female screw being threadably engaged with each other.

4. The apparatus according to claim 1, wherein said vibration transmitting means includes means for detachably connecting said vibration transmitting means to said connecting means.

5. The apparatus according to claim 4, wherein said vibration transmitting means includes one of a male screw and a female screw, and said connecting means includes the other one of said male screw and said female screw, said male screw and said female screw being threadably engaged with each other.

6. The apparatus according to claim 1, wherein said vibration transmitting means and said amplifying means are connected together such that said central axes of said connecting means and of said vibration transmitting means intersect at an angle between 5 degrees and 60 degrees.

7. The apparatus according to claim 6, wherein said vibration transmitting means and said amplifying means are connected together such that said central axes of said connecting means and of said vibration transmitting means intersect at an angle between 10 degrees and 45 degrees.

8. The apparatus according to claim 1, wherein said vibration transmitting means includes a proximal end portion and said connecting means includes a distal end portion, said proximal end portion of said vibration transmitting means having a smaller diameter than the diameter of said distal end portion of said connecting means, and wherein said vibration transmitting means and said amplifying means both include an outer surface, said connecting means including a cylindrical portion for connecting said vibration transmitting means to said outer surface of said amplifying means.

9. The apparatus according to claim 1, wherein a maximum amplitude of said loop portion lies approximately at said intersection point.

10. An ultrasonic treatment apparatus comprising:
    ultrasonic vibration generating means for generating ultrasonic vibration having nodes and loop portions between adjacent nodes;
    amplifying means having a distal end and a central axis, for amplifying said ultrasonic vibration generated by said ultrasonic vibration generating means;
    vibration transmitting means having a proximal end and a central axis, for transmitting said ultrasonic vibration amplified by said amplifying means to objective parts of living bodies; and
    a connecting member having a proximal end and a distal end, for connecting said vibration transmitting means to said amplifying means;
    said proximal end of said connecting member being connected to said distal end of said amplifying means in a region where a loop portion of said ultrasonic vibration lies; and
    said proximal end of said vibration transmitting means being connected to said distal end of said connecting member in said region where said loop portion of said ultrasonic vibration lies, such that said central axes of said vibration transmitting means and of said amplifying means intersect with each other at a predetermined angle at an intersection point, said intersection point being in said region of said loop portion of said ultrasonic vibration.

11. The apparatus according to claim 10, wherein said connecting member includes means for detachably connecting said connecting member to said amplifying means.

12. The apparatus according to claim 11, wherein said connecting member includes one of a male screw and a female screw, and said amplifying means includes the other one of said male screw and said female screw, said male screw and said female screw being threadably engaged with each other.

13. The apparatus according to claim 10, wherein said vibration transmitting means includes means for detachably connecting said vibration transmitting means.

14. The apparatus according to claim 13, wherein said vibration transmitting means includes one of a male screw and a female screw, and said connecting member includes the other one of said male screw and said female screw, said male screw and said female screw being threadably engaged with each other.

15. The apparatus according to claim 10, wherein said vibration transmitting means and said amplifying means are connected together such that said central axes of said connecting member and of said vibration transmitting means intersect an angle at between 5 degrees and 60 degrees.

16. The apparatus according to claim 15, wherein said vibration transmitting means and said amplifying means are connected together such that said central axes of said connecting member and of said vibration transmitting means intersect at an angle between 10 degrees and 45 degrees.

17. The apparatus according to claim 10, wherein said vibration transmitting means includes a proximal end portion and said connecting member includes a distal end portion, said proximal end portion of said vibration transmitting means having a smaller diameter that the diameter of said distal end portion of said connecting means, and wherein said vibration transmitting means and said amplifying means both include an outer surface, said connecting means including a cylindrical portion for connecting said vibration transmitting means to said outer surface of said amplifying means.

18. The apparatus according to claim 10, wherein said connecting member includes a proximal end portion formed with a male screw and a distal end portion formed with a female screw, said female screw being formed at a predetermined angle with respect to said male screw.

19. The apparatus according to claim 10, wherein said connecting member has a proximal end portion formed with a first male screw and a distal end portion formed with a second male screw, said second male screw being formed at a predetermined angle with said first male screw.

20. The apparatus according to claim 10, wherein said amplifying means includes a distal face inclined with respect to a plane perpendicular to said central axis of said amplifying means.

21. The apparatus according to claim 10, wherein said connecting member includes one of a distal face and a proximal face, said face being inclined with respect to a plane perpendicular to said central axis of said connecting member.

22. The apparatus according to claim 10, further comprising a vibrator cover surrounding said ultrasonic vibration generating means, said vibrator cover being made of electrically insulating material, and a sheath surrounding said vibration transmitting means, said sheath being made of electrically insulating material.

23. The apparatus according to claim 10, wherein a maximum amplitude of said loop portion lies approximately at said intersection point.

* * * * *

UNITED STATES PATENT AND TRADEMARK OFFICE
CERTIFICATE OF CORRECTION

PATENT NO. : 5,222,937
DATED : June 29, 1993
INVENTOR(S) : Hiroaki Kagawa

It is certified that error appears in the above-indentified patent and that said Letters Patent is hereby corrected as shown below:

Title Page: item [57]

In the Abstract, Line 15,

"connection" should be --connecting--.

Signed and Sealed this

Seventh Day of November, 1995

Attest:

BRUCE LEHMAN

*Attesting Officer*    Commissioner of Patents and Trademarks